(12) United States Patent
Fay

(10) Patent No.: US 11,610,770 B1
(45) Date of Patent: Mar. 21, 2023

(54) UV RADIATION SOURCE ASSEMBLY

(71) Applicant: Trojan Technologies Group ULC, London (CA)

(72) Inventor: Patrick Alexander Fay, London (CA)

(73) Assignee: Trojan Technologies Group ULC, London (CA)

( * ) Notice: Subject to any disclaimer, the term of this patent is extended or adjusted under 35 U.S.C. 154(b) by 0 days.

(21) Appl. No.: 17/752,157

(22) Filed: May 24, 2022

Related U.S. Application Data

(60) Provisional application No. 63/255,164, filed on Oct. 13, 2021.

(51) Int. Cl.
 *H01J 61/36* (2006.01)
 *C02F 1/32* (2023.01)
 *A61L 2/08* (2006.01)
 *H01J 5/60* (2006.01)

(52) U.S. Cl.
 CPC .............. *H01J 61/366* (2013.01); *A61L 2/08* (2013.01); *C02F 1/325* (2013.01); *H01J 5/60* (2013.01); *H01J 61/36* (2013.01)

(58) Field of Classification Search
 CPC . H01J 61/36; H01J 61/366; H01J 5/60; A61L 2/08; C02F 1/325
 USPC ...................................................... 313/318.2
 See application file for complete search history.

(56) References Cited

U.S. PATENT DOCUMENTS

| 6,500,346 | B1 | 12/2002 | Taghipour et al. |
| 7,033,203 | B2 | 4/2006 | Titchener |
| 7,390,222 | B2 | 6/2008 | Ciancanelli et al. |
| 7,390,225 | B2 | 6/2008 | Elku et al. |
| 8,167,654 | B2 | 5/2012 | Elku et al. |
| 8,318,007 | B2 | 11/2012 | Fraser et al. |
| 8,338,808 | B2 | 12/2012 | Fraser et al. |
| 8,866,105 | B2 | 10/2014 | Strik et al. |
| 9,155,808 | B2 | 10/2015 | Moglan et al. |

(Continued)

FOREIGN PATENT DOCUMENTS

CN          2915839 Y          6/2007

OTHER PUBLICATIONS

Jan. 6, 2023 International Search Report issued in International Patent Application No. PCT/IB2022/059749.

(Continued)

*Primary Examiner* — Christopher M Raabe

(57) ABSTRACT

A radiation source assembly comprises a source base, a UV transparent sleeve, and a UV lamp. The source base comprises a sealed electrical connection interface and an opposing sealed sleeve interface. The sealed electrical connection interface comprises a electrical contacts and the sealed sleeve interface comprise a radial sealing element, an outer collar, and a compression ring. The UV transparent sleeve is engaged with the sleeve interface such that the radial sealing element of the sealed sleeve interface is disposed between the UV transparent sleeve and the outer collar of the source base, and the compression ring is positioned over the UV transparent sleeve and engaged with the source base to compress the radial sealing element onto the UV transparent sleeve and the outer collar. The UV lamp is disposed within the UV transparent sleeve and electrically coupled to the electrical contacts of the electrical connection interface.

17 Claims, 8 Drawing Sheets

(56) References Cited

U.S. PATENT DOCUMENTS 9,856,153 B2    1/2018  Penhale
2011/0227473 A1* 9/2011  Elku .................. C02F 1/325
                                                313/243

OTHER PUBLICATIONS

Jan. 6, 2023 Written Opinion issued in International Patent Application No. PCT/IB2022/059749.

* cited by examiner

UV RADIATION SOURCE ASSEMBLY

FIELD

This application relates generally to the field of electrical connections, and, more particularly, to an electrical connection system for a sealed ultraviolet radiation source assembly.

BACKGROUND

Ultraviolet light-based fluid treatment systems employ ultraviolet (UV) radiation lamps to emit radiation of a particular wavelength or range of wavelengths (usually between 185 and 400 nm) to kill, sterilize and/or prevent replication of microorganisms (bacteria, viruses, pathogens and the like) that may be present in fluids, such as municipal or industrial water treatment, or municipal wastewater treatment. To do so, however, the UV lamps and their corresponding electrical connections, are immersed in the fluids/water being treated. Conventional ultraviolet radiation lamps include low pressure lamps, medium pressure lamps, low pressure high output lamps and the like.

It has become conventional to use such ultraviolet lamps configured to have all of the electrical connections disposed at one end of the lamp. See, for example, FIGS. 2-8 of U.S. Pat. No. 4,700,101 Ellner, et al. (Ellner) and FIGS. 1, 2 and 4 of U.S. Pat. No. 5,166,527 Solymar. As can be seen from the conventional radiation lamps taught by Ellner and Solymar, the electrical connection pins are elongate and are disposed such that the axes of the pins are parallel with the longitudinal axes of radiation lamp. In other words, the electrical connection is made by pushing an end cap or other connection base on to the pins in a direction parallel to the longitudinal axis of the radiation lamp.

A problem with this approach is that in many applications, the radiation lamp is immersed in a flow of water and turbulence created within that water treatment system invariably imparts a vibratory motion to the lamps which frequently results in lamps being vibrated or shaken loose of its electrical connection base or socket thereby causing the lamps to be rendered completely or intermittently inoperative. When such an event occurs, the water being treated may not be fully disinfected.

Slant based lamp assemblies have been developed which advantageously address these issues. See, for example, U.S. Pat. No. 8,167,654 to Elku et al., the entirety of which is incorporated by reference. In Elku, connector pins are disposed at an oblique angle with respect to a longitudinal axis of a UV lamp. When the lamp is plugged into a radiation module, a protective quartz sleeve is installed over the lamp and lamp connector/radiation module connection. Because the quartz sleeve does not allow the lamp and lamp connector to move along the oblique angle, the lamp does not vibrate into disengagement. While advantageous in many respects, field replacement of such lamps, including re-assembly with UV-transparent quartz sleeves and their securing and sealing devices, may lead to contamination, loss of watertight integrity, and degradation of sanitization performance. This is because the quartz sleeves cannot provide protection to the UV lamp or its connection to a radiation module until the quartz sleeve is installed on the radiation module.

There remains the need for a lamp device, particularly a UV radiation lamp, which will provide a reliable electric connection, and improved system integrity in submerged water treatment environments, including after field replacement of the lamps.

SUMMARY

A radiation source assembly for use in connection with a radiation module having a receptacle connector comprises a source base, a UV transparent sleeve, and a UV lamp. The source base comprises a sealed electrical connection interface and an opposing sealed sleeve interface. The sealed electrical connection interface comprises a plurality of electrical contacts and the sealed sleeve interface comprise a radial sealing element, an outer collar, and a compression ring. The UV transparent sleeve is engaged with the sleeve interface such that the radial sealing element of the sealed sleeve interface is disposed between the UV transparent sleeve and the outer collar of the source base, and the compression ring is positioned over the UV transparent sleeve and engaged with the source base to compress the radial sealing element onto the UV transparent sleeve and the outer collar of the source base. The UV lamp is disposed within the UV transparent sleeve and electrically coupled to the electrical contacts of the electrical connection interface.

The radiation source assembly may further comprise a retaining device that is located over the source base to mechanically couple the source base to the receptacle connector when the electrical connection interface is fully engaged with the receptacle connector.

In some embodiments, the sleeve interface further comprises: an O-ring disposed between the UV transparent sleeve and an outer collar of the source base; and a compression ring over the UV transparent sleeve and engaged with the source base to compress the O-ring onto the UV transparent sleeve and the outer collar of the source base. The compression ring may further comprise a plurality of protrusions 25a which lockingly engage with apertures on the outer collar of the source base. The sleeve interface may further comprise a sleeve cushion between the UV transparent sleeve and the source base.

In some embodiments, the sealed electrical connection interface comprises a cylindrical structure extending from the source base having a radial sealing element disposed on an outer surface thereof, with the plurality of electrical contacts located within an inner diameter the cylindrical structure. The sealed electrical connection interface may further comprise at least one electrical barrier between at least two of the plurality of electrical contacts. The plurality of electrical contacts may be selected from a group consisting of electrically conductive pins and electrically conductive sockets.

In some embodiments, the radiation source assembly further comprises a support device connected between the source base and the UV lamp, wherein the support device maintains fixed spatial and orientation relationship between the source base and the UV lamp.

In some embodiments, the electrical connection interface is disposed at an oblique angle with respect to a longitudinal direction of the radiation source assembly, for example, about fifteen degrees.

The retaining device may be selected from the group consisting of a threaded fastener, a bayonet fastener, and a snap fastener.

According to another aspect of the invention, a source base for use in connection with a radiation module having a receptacle connector comprises a sealed electrical connection interface and an opposing sealed sleeve interface, the sealed electrical connection interface comprising a plurality of electrical contacts. In some embodiments, the sealed sleeve interface comprising a radial sealing element, an outer collar, and a compression ring.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The illustrated example embodiments will be best understood by reference to the figures. The following description is intended only by way of example, and simply illustrates certain example embodiments.

Figure 1:
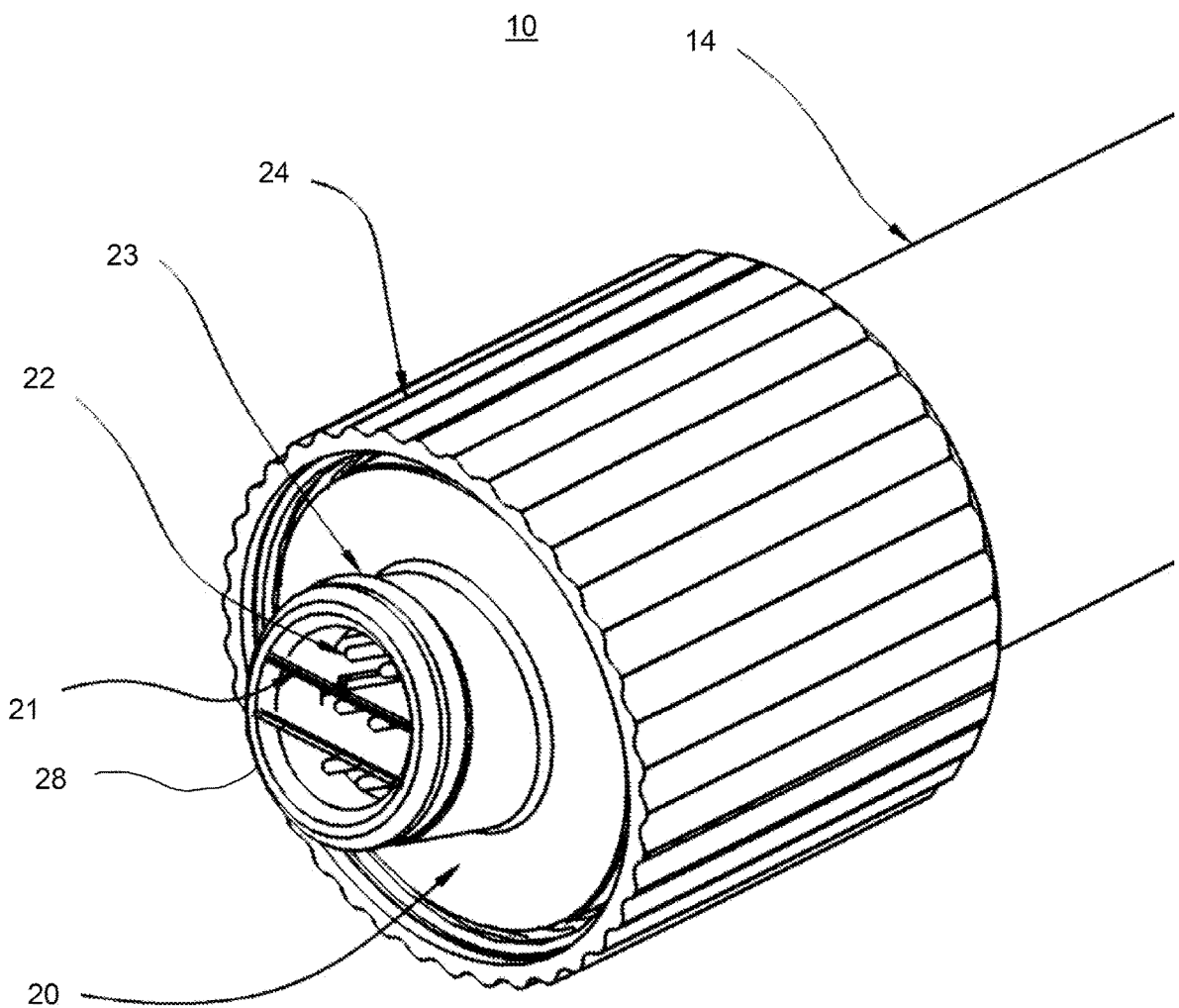
FIG. 1 illustrates an example embodiment of a source base of a radiation source assembly.
Figure 5:
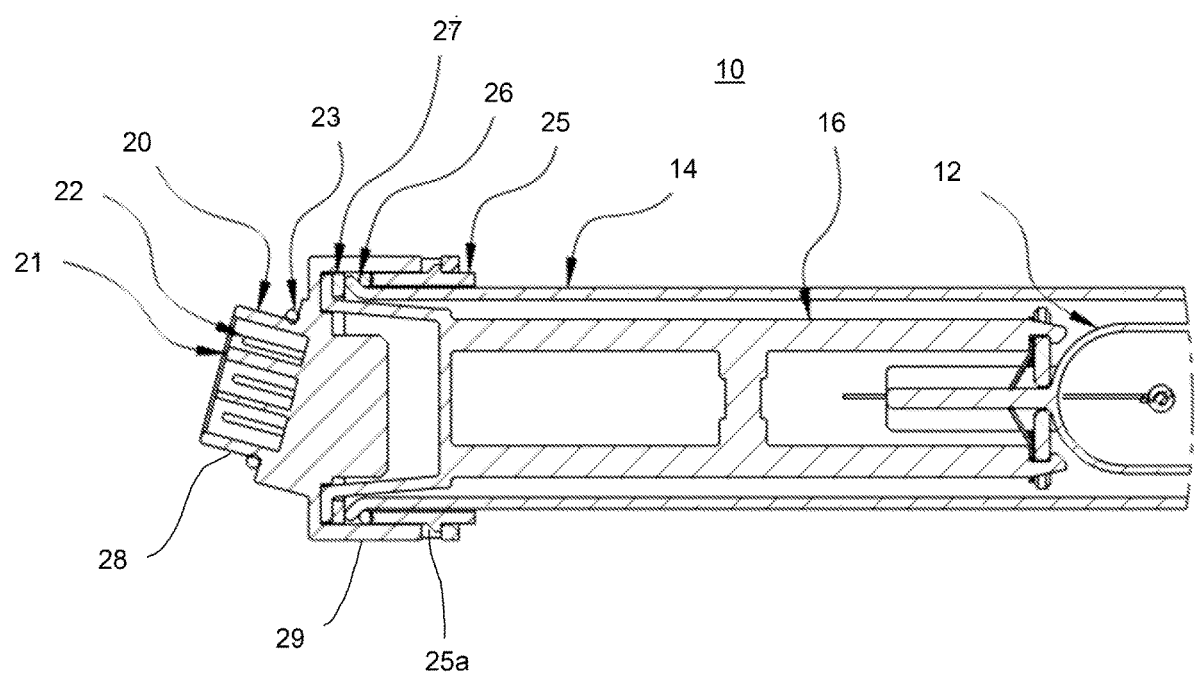
FIG. 5 illustrates a cutaway view of an example embodiment of a radiation source assembly.

A sealed radiation source assembly 10 is provided herein. Referring for example to FIGS. 1 and 5, the radiation source assembly 10 comprises a UV radiation lamp 12, a UV transparent sleeve 14, and a source base 20. In some embodiments, the source base 20 comprises a sealed sleeve interface and an electrical interface on a side opposite of the sleeve interface. The UV transparent sleeve 14 may be a quartz sleeve. UV transparent sleeves are often employed to thermally isolate UV layers from water undergoing treatment so that the lamp can achieve proper operating temperature.

The source base 20 may be employed at the end of any suitable structure and the quartz sleeve is not intended to be a limiting example. For example, the source base 20 may be at the end of any type of lamp to be plugged into a receiving socket, or the source base 20 may be on any device requiring electrical or communication connection. If, for example, no sleeve is required, the source base can be integrated into a lamp base.

In an embodiment, the electrical interface of the source base 20 has electrical contacts 22. The electrical interface including the electrical contacts 22 extend from one end of the radiation source assembly. The electrical contacts 22 may be pins, tabs, sockets, or the like. The electrical contacts 22 may transfer electrical power from a power source to the radiation lamp 12. In some embodiments, the electrical contacts may control and/or provide feedback to the lamp.

In an embodiment, the electrical interface includes electrical barriers 21 between some of the electrical contacts 22. For example, a ridge of non-conductive material may be placed between one or more of the electrical contacts. The electrical barrier may serve to electrically isolate electrical contacts, help to guide proper mating of the electrical connection, or the like.

In some embodiments, the sealed electrical interface is further provided with additional features that are placed on an oblique angle relative to the central axis of the radiation source assembly 10. In such embodiments, the angled features of the sealed electrical interface includes not only the angled electrical contacts, but one or more non-conductive alignment and/or sealing structures extending from the radiation source assembly 10. A radiation module into which the radiation source assembly 10 is to be installed has a correspondingly angled and featured receptacle. This angled electrical interface prevents the radiation source assembly 10 from being fully secured to a radiation module assembly unless the electrical interface is fully seated in the mating receptacle. As used herein, "radiation module" and "radiation module assembly" refers to a frame or other structure of a water treatment system that mechanically and electrically supports a plurality of radiation lamps/assemblies. Proper and sound electrical connection is made before mechanically fastening the UV radiation source assembly to a radiation module leg. In an embodiment, a mechanical indication may be provided that a lamp is not properly installed as a retaining device 24 will not thread onto a radiation module leg coupling.

In some embodiments, the electrical interface includes an O-ring 23 disposed on a cylindrical structure 28 extending from source base 20. The O-ring is disposed on an outer surface of the cylindrical structure and the electrical contacts 22 are disposed within an inner circumference of the cylindrical structure. Such an arrangement when combined with a complementary receptacle has the benefit of the sealing action being independent of the amount of compression generated by the retaining device 24. Alternatively or additionally, a seal may be a face seal, radial seal or deformable element.

In an embodiment, a retaining device 24 may be used to complete, tighten, maintain, or align the connection between the radiation source assembly and a corresponding radiation module. The cap or retaining device 24 may be a threaded ring that fits over and around the UV transparent sleeve 14. The threading of the retaining device 24 completes and maintains the connection and may give a mechanical indication of when a connection is fully secured. In some embodiments, the retaining device may also be a bayonet fastener, snap fastener, or the like. As set forth above, the obliquely angled features of the electrical interface, and its corresponding radiation module receptacle, prevent the retaining device 24 from threading onto or otherwise engaging a complementary feature on the radiation module receptacle until the electrical interface is fully seated in the receptacle. This avoids having to rely on the clamping force provided by the retaining device 24 for electrical contact and sealing and greatly enhancing system reliability In an embodiment, the electrical contacts may be at an angle or canted from the centerline of the UV transparent sleeve 14. The angle may be greater than zero degrees and less than ninety degrees. In an embodiment, the electrical pins 22, electrical barriers 21, and/or cylindrical structure 28 of the electrical interface may be at an angle of fifteen degrees from the UV transparent sleeve 14 centerline.

Figure 2:
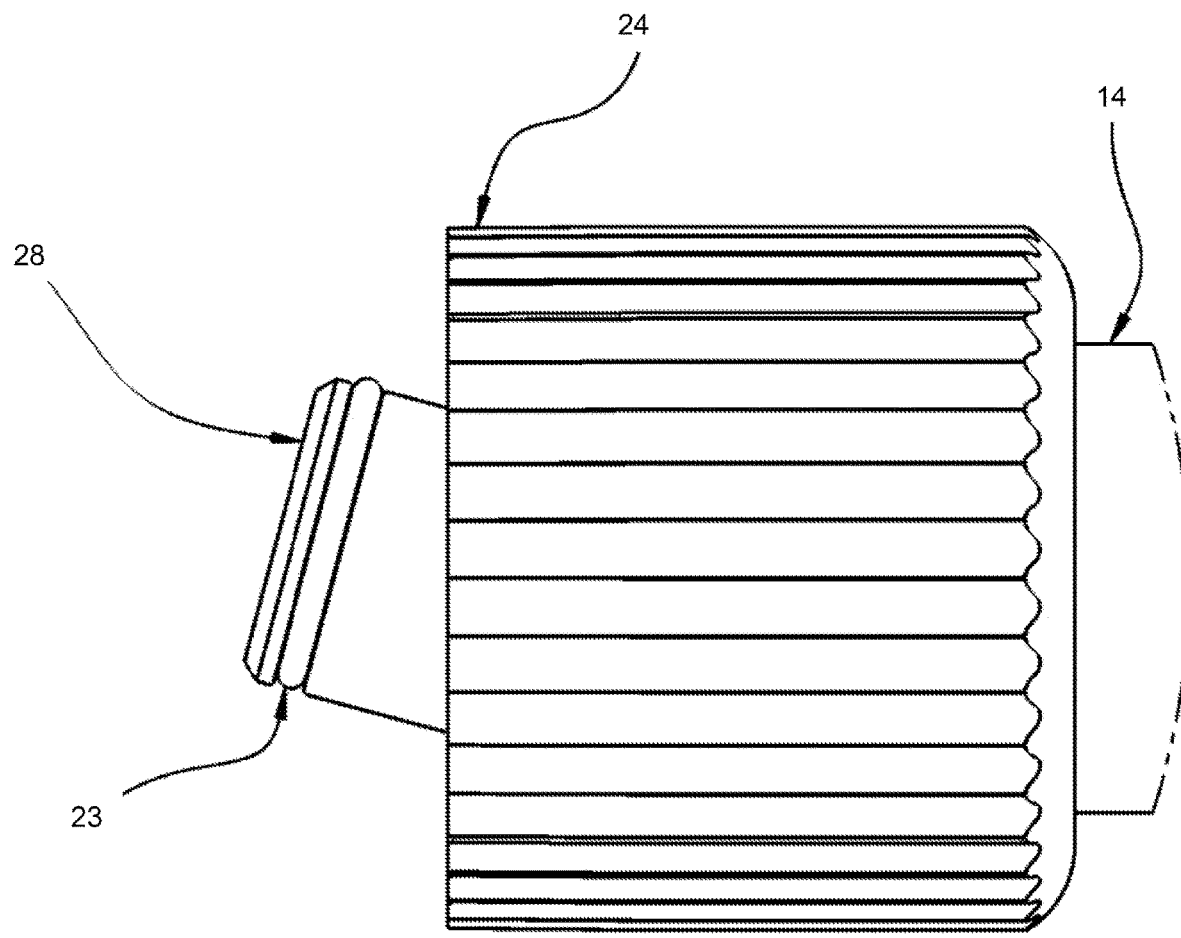
FIG. 2 illustrates another view of the source base of FIG. 1.

Referring to FIG. 2, in an embodiment, a side view of a source base 20 is illustrated. In the illustrated embodiment, the source base 20 is located at and attached to the end of a UV transparent sleeve 14. In the illustrated example, a distal end of the source base 20 opposite the UV transparent sleeve 14 is angled or canted from the centerline of the UV transparent sleeve 14. The distal end or electrical connection end of the source base 20 includes electrical contacts. Near the distal end of the source base 20 there may be an O-ring 23 to provide a seal for the electrical contacts and/or to provide a secure connection. In an embodiment, the source base 20 may be tapered or shaped at the distal end to allow guidance of the insertion of the source base 20 into a receptacle on a radiation module. The source base 20 may be inserted into a radiation module leg, and complete an electrical circuit. In an embodiment, the retaining device 24 is around the UV transparent sleeve 14 and, when tightened, exerts clamping force on the source base 20 in line with a center axis of the radiation source assembly. The retaining device 24 may be a ring with an inside diameter greater than the outside diameter of the UV transparent sleeve 14. The retaining device 24 may slide freely for at least a portion of the distance along the UV transparent sleeve 14. The retaining device 24 may have a thread, snap, or the like. The retaining device 24 may affix, clamp, secure, or the like the source base 20 to a radiation module leg. The retaining device 24 may have ridges, nubs, or the like to provide an area for gripping and tightening the retaining device 24. In an embodiment, retaining device 24 may have different configurations (see FIG. 3). In an embodiment, the retaining device 24 may provide a mechanical reference to a user that the connection is fully secure, in other words, that the source base 20 and radiation module leg are properly connected and/or seated fully.

Figure 3:
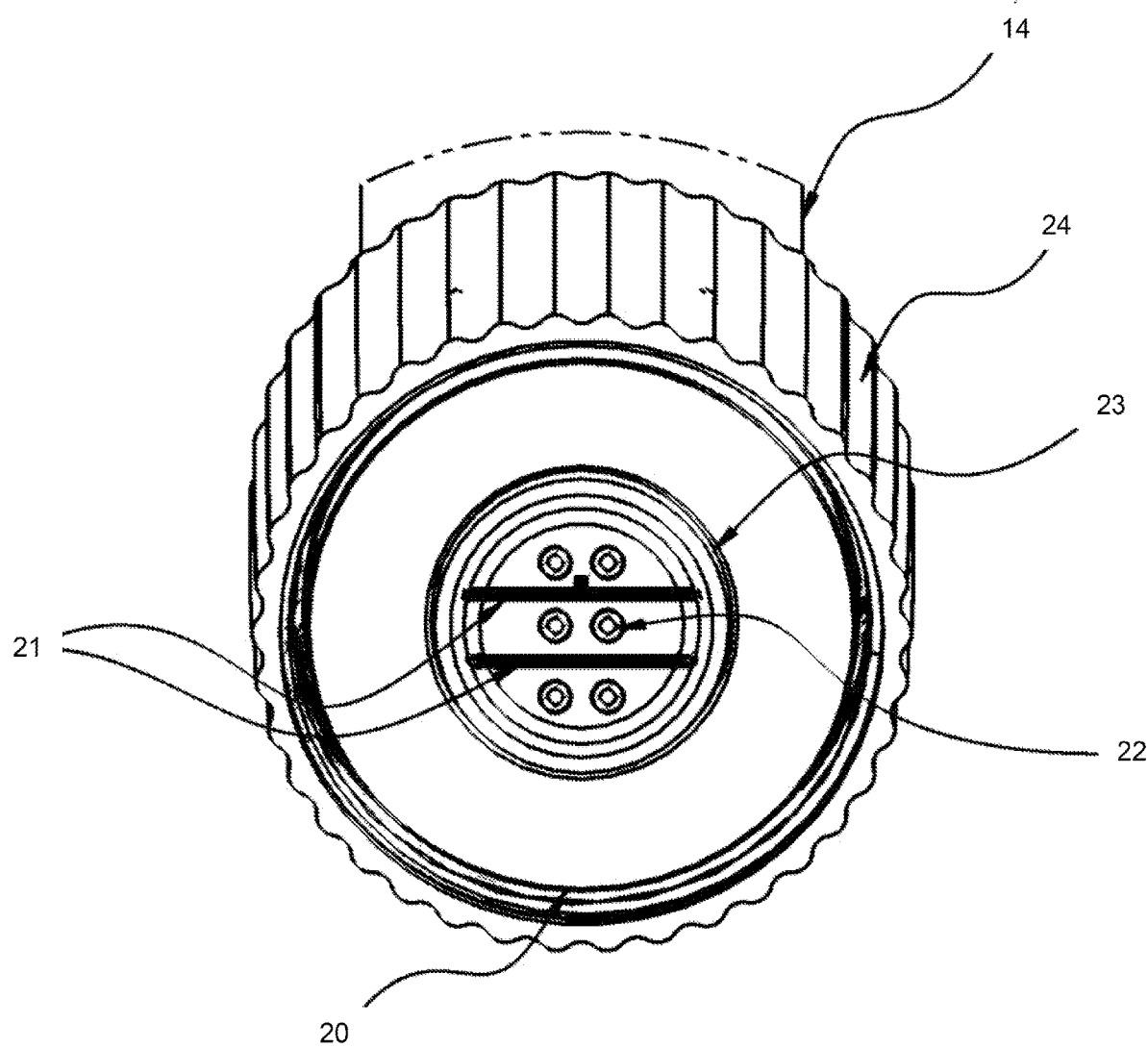
FIG. 3 illustrates another view of the source base of FIG. 1.

Referring to FIG. 3, in an embodiment, an elevated end view of the source base 20 is illustrated. In an embodiment, the source base 20 may have electrical contacts 22 at an angle to the UV transparent sleeve 14. This view is from the perspective of viewing the electrical pins head on, thus the UV transparent sleeve 14 is angled in the background. Also featured is the O-ring 23 and retaining device 24. Additionally or alternatively, there may be a face seal in an area between the electrical pins and the cap. In an embodiment, electrical barriers 21 may be present. The electrical barriers may provide a barrier between at least two electrical contacts and/or may assist with proper alignment of the source base 20 to a radiation module leg.

Figure 4:
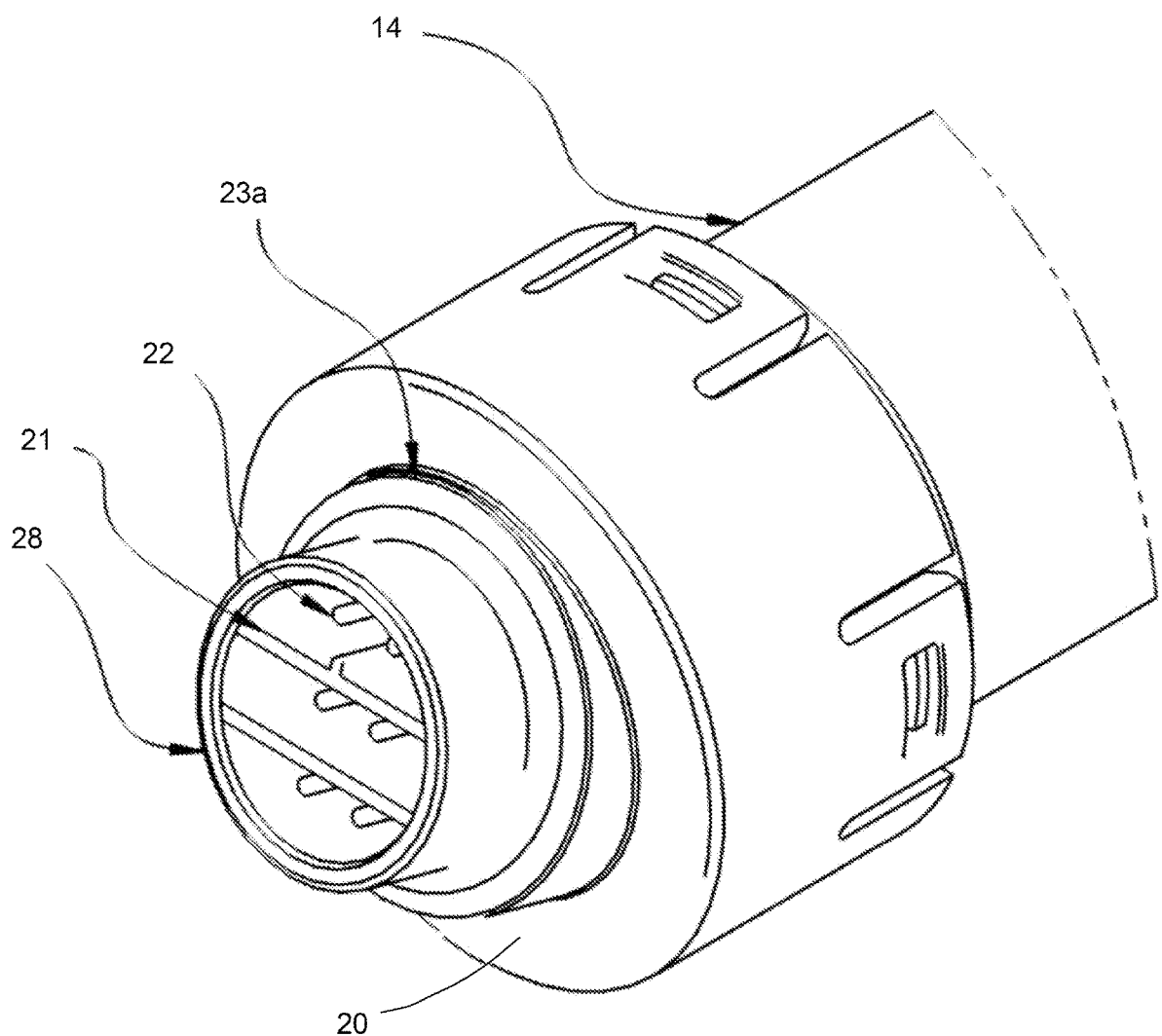
FIG. 4 illustrates certain aspects of the source base of FIG. 1.

Referring to FIG. 4, in an embodiment, another view of a source base 20 is illustrated. In an embodiment, the source base 20 at the end of the UV transparent sleeve 14 is illustrated with associated electrical barrier 21 and electrical contacts 22 as described herein. In an embodiment, the source base 20 may have a face seal or crush style O-ring 23a for sealing electrical contacts. In other words, the retaining device 24 draws the source base 20 and radiation module leg together and may crush or compress a face seal to provide a seal.

Referring to FIG. 5, in an embodiment, a cutaway view of a source base 20 is illustrated. In an embodiment, the source base 20 may fit over a UV transparent sleeve 14. The UV transparent sleeve 14 may have a support device 16 for the ultraviolet lamp 12. Also illustrated are the electrical barriers 21, electrical contacts 22, crush style O-ring 23a described herein.

Figure 8:
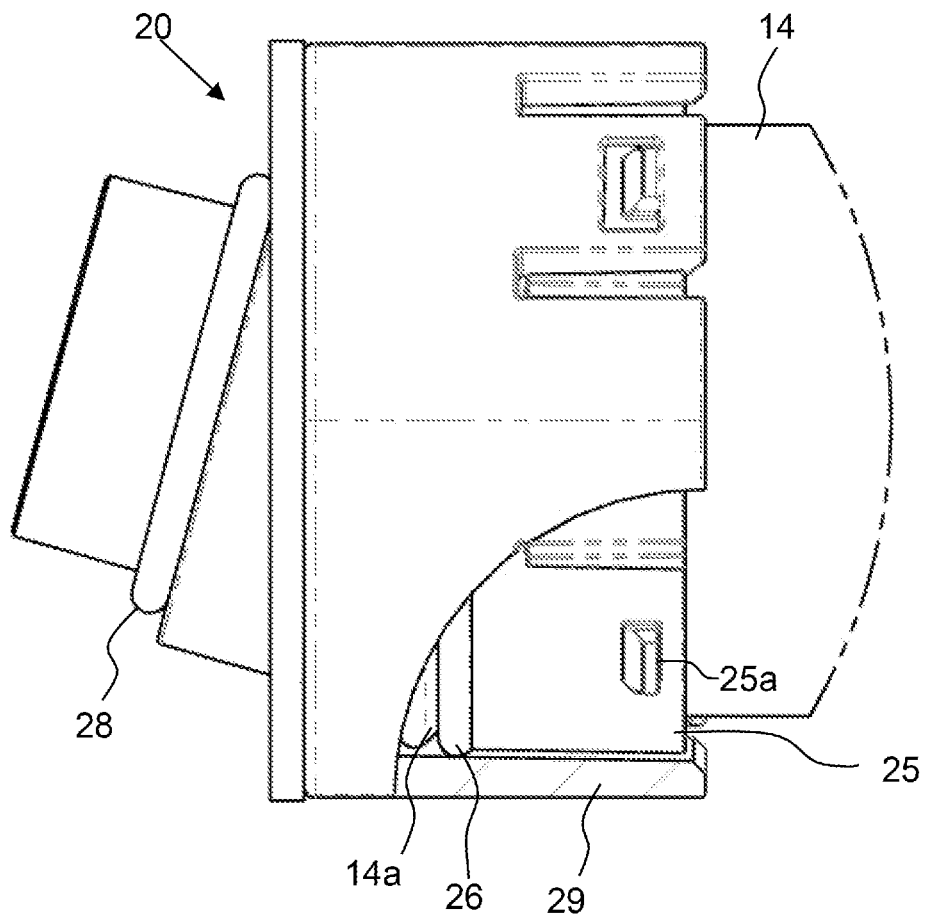
FIG. 8 illustrates a partial cutaway view of an source base for a radiation source assembly.

Referring to FIGS. 5 and 8, in some embodiments, the sleeve interface of the source base 20 comprises a compression ring 25, an outer collar 29 disposed on the source base 20 and a sealing element, such as O-ring 26. The compression ring 25, outer collar 29 and O-ring 26 may comprise a sleeve sealing means. The compression ring 25 is between the UV transparent sleeve 14 and the outer collar 29, which fits over the UV transparent sleeve 14. In an embodiment, the UV transparent sleeve includes an out-turned lip 14a. In an embodiment, the device may have a sleeve cushion 27 to support the UV transparent sleeve 14.

Compression ring 25 is inserted into source base 20 and contacts the O-ring 26. As the O-ring 26 is compressed against the lip of the UV transparent sleeve 14, compression ring 25 also compresses the lip against the sleeve cushion 27. When fully inserted, protrusions 25a project through apertures on the outer collar 29 of the source base 20 and lock the compression ring 25 in place. This arrangement provides a reliable, watertight seal that may be assembled at a manufacturing facility located remotely from a water treatment facility, thereby avoiding reliance on field personnel to seal lamp enclosures without introducing contamination or moisture.

Also illustrated is an ultraviolet (UV) radiation lamp 12. In some embodiments, the UV radiation lamp 12 has a ceramic base. In some embodiments, the UV radiation lamp 12 has an electrode at each end of a tubular structure, mercury bound into amalgam and disposed within the tubular structure, and an inert gas. A lamp arc is defined by the distance between the electrodes.

Support device 16 engages both the source base 20 and the ceramic base of the UV radiation lamp 12. Support device 16 fixes the orientation of the UV radiation lamp 12 with respect to the source base 20 both rotationally and longitudinally. This ensures accurate location of the filaments and (and therefore the lamp arc) in position for optimal performance.

In some embodiments, a foot or base of the support device 16 is positioned between the sleeve cushion 27 and the source base outer collar 29 as illustrated in FIG. 5. Advantageously, the support device 16 is locked into place with the insertion of the compression ring 25 into the outer collar 29 at the same time that the UV transparent sleeve 14 is engaged within the sleeve interface.

Wires (not shown) couple electrical connector pins 22 to the UV radiation lamp 12. The support device 16 may also support and provide physical separation to the wires to reduce the potential for arcing. Moving electrical contacts 22 off of the ceramic lamp base and into source base 20 improves manufacturability and electrical reliability.

In some embodiments, an inner portion of the source base is filled with a potting compound after the electrical pins and related wiring are installed. This isolates the radiation module into which the radiation source assembly 10 is installed from suffering water damage and/or creating an electrical hazard in the event of UV transparent sleeve failure, or failure of the O-ring 26.

Figure 6:
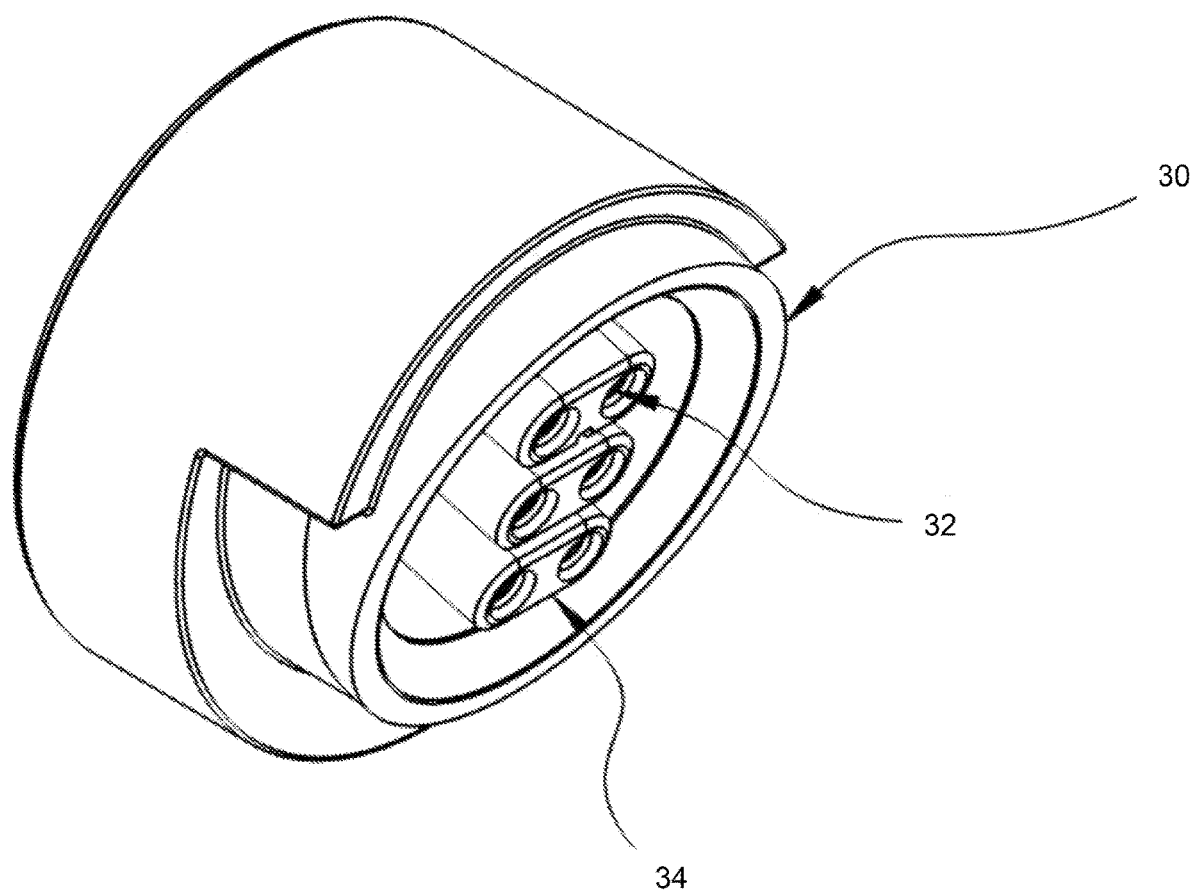
FIG. 6 illustrates an example embodiment of a receptacle on a radiation module corresponding to a source base of a radiation source assembly.

Referring to FIG. 6, in an embodiment, an example of a module receptacle connector 30 for engaging source base 20 is illustrated. In an embodiment, the module receptacle connector 30 may have features as illustrated including electrical contacts 32 and electrical contact supports 34. In an embodiment, the electrical contacts 32 may be sockets. In an embodiment, the electrical contacts may be sockets, pins, or a combination thereof. In some embodiments, the module receptacle connector 30 includes a potting compound to prevent water intrusion into the radiation module frame (and wiring) in the event of seal failure. In an embodiment, there may be raised contact supports 34 for electrical contacts and orientation or alignment of electrical contacts or connections. In other words, many configurations for the angled or canted electrical contacts or connections are contemplated and disclosed. The mating surface of the module receptacle connector 30 to a radiation module may be complementary in many configurations.

Figure 7:
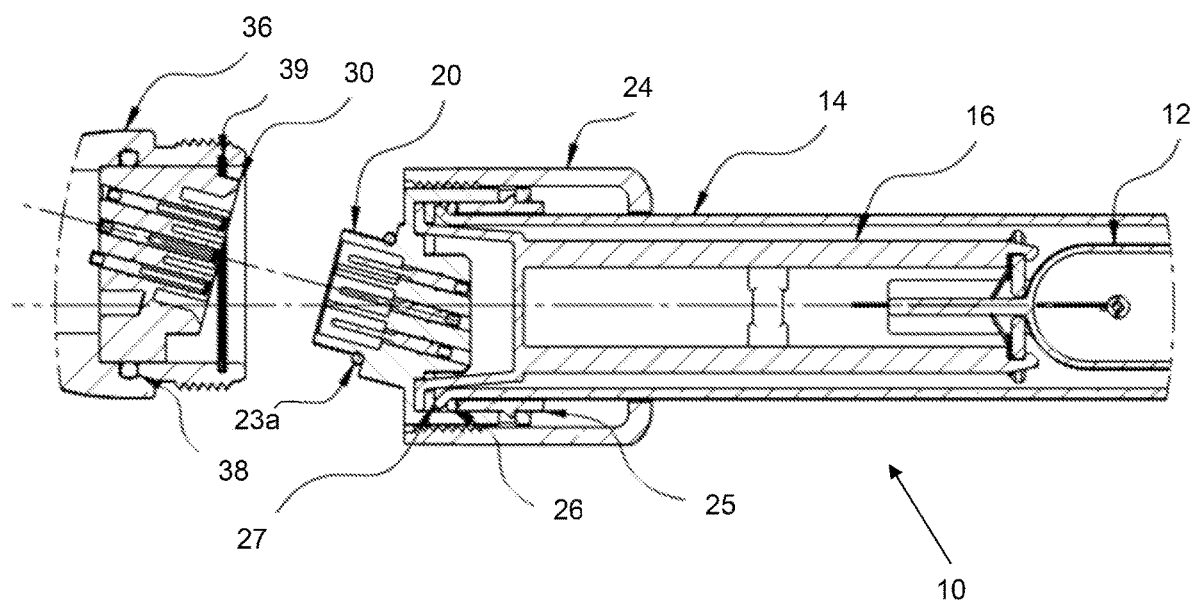
FIG. 7 illustrates a cutaway view of an example embodiment of a radiation source assembly and source base.

Referring to FIG. 7, in an embodiment, a module receptacle connector 30 may be complementary for a connection of a radiation source assembly 10 to a radiation module. In other words, in some embodiments, the source base 20 is a plug, and the module receptacle connector 30 is a corresponding socket. These features may be reversed, however, it is generally safer to have the socket on the radiation module. The receptacle connector 30 also has non-electrical features complementary to, for example, electrical barriers 21 and/or cylindrical portion 28

Also illustrated are retaining device 24, an O-ring 23*a* to seal electrical contacts, a sleeve cushion 27, a crush style O-ring 26 to seal the radiation source assembly 10, a compression ring 25, a UV transparent sleeve 14, a support device 16 for the UV radiation lamp 12. In an embodiment, the module receptacle connector 30 may be part of radiation module leg coupling 36. The radiation module leg coupling 36 may accept and mate with the retaining device 24, such as in threaded engagement. For example, a threaded, snap, or similar connection may be made. In an embodiment, there may be a radial seal O-ring 38 to seal an interface between the plug and radiation module leg coupling. In an embodiment, there may be a snap or retaining ring 39 to axially secure the module receptacle connector 30 within the radiation module coupling 36. In some embodiments, the radiation module leg coupling 36 and module receptacle connector 30 are indexed with anti-rotation features, such as an index point or a flattened surface.

The various embodiments described herein thus represent a technical improvement to conventional electrical connectors. Using the techniques as described herein, an embodiment may use a device and method to attach a source base 20 of an ultraviolet radiation source assembly to a radiation module base. In an embodiment, the electrical pins, sockets, or the like are angled or canted from the longitudinal axis of the ultraviolet lamp or other device to be connected. This is in contrast to conventional methods with limitations mentioned above. Such techniques provide a better device and method to ensure a proper electrical connection.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A radiation source assembly for use in connection with a radiation module having a receptacle connector, comprising:
    a source base comprising a sealed electrical connection interface and an opposing sealed sleeve interface, the sealed electrical connection interface comprising a plurality of electrical contacts, and the sealed sleeve interface comprising a radial sealing element, an outer collar, and a compression ring;
    a UV transparent sleeve engaged with the sleeve interface such that the radial sealing element of the sealed sleeve interface is disposed between the UV transparent sleeve and the outer collar of the source base, and the compression ring is positioned over the UV transparent sleeve and engaged with the source base to compress the radial sealing element onto the UV transparent sleeve and the outer collar of the source base; and
    a UV lamp disposed within the UV transparent sleeve and electrically coupled to the electrical contacts of the electrical connection interface.

2. The radiation source assembly of claim 1, wherein the electrical connection interface is disposed at an oblique angle with respect to a longitudinal direction of the radiation source assembly.

3. The radiation source assembly of claim 2, wherein the oblique angle is about fifteen degrees.

4. The radiation source assembly of claim 1, further comprising a retaining device located over the source base to mechanically couple the source base to the receptacle connector when the electrical connection interface is fully engaged with the receptacle connector.

5. The radiation source assembly of claim 1, wherein the radial sealing element comprises an O-ring.

6. The radiation source assembly of claim 1, wherein the compression ring further comprises a plurality of protrusions which lockingly engage with apertures on the outer collar.

7. The radiation source assembly of claim 1, wherein the sleeve interface further comprises a sleeve cushion between the UV transparent sleeve and the source base.

8. The radiation source assembly of claim 1, wherein the sealed electrical connection interface further comprises a cylindrical structure extending from the source base having a radial sealing element disposed on an outer surface thereof, with the plurality of electrical contacts located within an inner diameter of the cylindrical structure.

9. The radiation source assembly of claim 1, wherein the sealed electrical connection interface further comprises at least one electrical barrier between at least two of the plurality of electrical contacts.

10. The radiation source assembly of claim 1, wherein the plurality of electrical contacts are selected from the group consisting of electrically conductive pins and electrically conductive sockets.

11. The radiation source assembly of claim 1 further comprising a support device connected between the source base and the UV lamp, wherein the support device maintains fixed spatial and orientation relationship between the source base and the UV lamp.

12. The radiation source assembly of claim 4, wherein the retaining device is selected from the group consisting of a threaded fastener, a bayonet fastener, and a snap fastener.

13. A radiation source assembly for use in connection with a radiation module having a receptacle connector, comprising:

a source base comprising a sealed electrical connection interface and an opposing sealed sleeve interface, the sealed electrical connection interface comprising a plurality of electrical contacts and the sealed sleeve interface comprising a sleeve sealing means;

a UV transparent sleeve engaged with the sleeve interface by the sleeve sealing means; and a UV lamp disposed within the UV transparent sleeve and electrically coupled to the electrical contacts of the electrical connection interface.

14. The radiation source assembly of claim 13, wherein the electrical connection interface is disposed at an oblique angle with respect to a longitudinal direction of the radiation source assembly.

15. The radiation source assembly of claim 13, further comprising a retaining device located over the source base to mechanically couple the source base to the receptacle connector when the electrical connection interface is fully engaged with the receptacle connector.

16. The radiation source assembly of claim 13, wherein the sealed electrical connection interface further comprises a cylindrical structure extending from the source base having a radial sealing element disposed on an outer surface thereof, with the plurality of electrical contacts located within an inner diameter of the cylindrical structure.

17. The radiation source assembly of claim 13, wherein the sleeve sealing means comprises a radial sealing element, an outer collar, and a compression ring.

* * * * *